United States Patent
Iida et al.

(10) Patent No.: US 12,159,148 B2
(45) Date of Patent: Dec. 3, 2024

(54) DIGITAL TWIN COMPUTING APPARATUS, DIGITAL TWIN COMPUTING METHOD, PROGRAM AND DATA STRUCTURE

(71) Applicant: NIPPON TELEGRAPH AND TELEPHONE CORPORATION, Tokyo (JP)

(72) Inventors: Yasuhiro Iida, Tokyo (JP); Ryutaro Kawamura, Tokyo (JP); Masayuki Hanadate, Tokyo (JP); Koya Mori, Tokyo (JP); Takao Nakamura, Tokyo (JP); Shigekuni Kondo, Tokyo (JP); Yukio Koike, Tokyo (JP); Hiroshi Ogawa, Tokyo (JP); Hiroshi Sakai, Tokyo (JP); Hiroyuki Tanaka, Tokyo (JP)

(73) Assignee: NIPPON TELEGRAPH AND TELEPHONE CORPORATION, Tokyo (JP)

(*) Notice: Subject to any disclaimer, the term of this patent is extended or adjusted under 35 U.S.C. 154(b) by 440 days.

(21) Appl. No.: 17/616,153

(22) PCT Filed: Jun. 7, 2019

(86) PCT No.: PCT/JP2019/022765
§ 371 (c)(1),
(2) Date: Dec. 2, 2021

(87) PCT Pub. No.: WO2020/246032
PCT Pub. Date: Dec. 10, 2020

(65) Prior Publication Data
US 2022/0253321 A1    Aug. 11, 2022

(51) Int. Cl.
*G06F 9/448*    (2018.01)

(52) U.S. Cl.
CPC .................................. *G06F 9/448* (2018.02)

(58) Field of Classification Search
None
See application file for complete search history.

(56) References Cited

U.S. PATENT DOCUMENTS

| 2017/0323240 A1* | 11/2017 | Johnson | .............. G06Q 10/04 |
| 2018/0039249 A1* | 2/2018 | Johnson | .............. G05B 17/02 |

(Continued)

FOREIGN PATENT DOCUMENTS

| JP | H07-036696 A | 2/1995 |
| JP | H11-250283 A | 9/1999 |

(Continued)

OTHER PUBLICATIONS

Shangguan et al. (2019) "A Hierarchical Digital Twin Model Framework for Dynamic Cyber-Physical System Design" ICMRE 2019, Feb. 16-19, 2019, Rome, Italy, pp. 123-129.

(Continued)

*Primary Examiner* — Adam Lee (57) ABSTRACT

The present invention includes a memory and a processor configured to store, in a storage, a first digital twin in which at least one model defining at least one function of an entity at a given time, and at least one piece of second data that includes, as a constituent element, first data for realizing the function of the entity due to being input to the model are included, create at least one second digital twin by performing predetermined first computation using, as a computation target, at least one first digital twin stored in the storage, and execute computation for arranging the second digital twin in a sandbox for which a predetermined time axis has been set, and realizing a function of an entity indicated by the second digital twin in the sandbox in accordance with the time axis.

20 Claims, 8 Drawing Sheets

(56) References Cited

U.S. PATENT DOCUMENTS

| | | | |
|---|---|---|---|
| 2018/0202892 A1* | 7/2018 | Vaskinn | G06F 30/20 |
| 2018/0203959 A1 | 7/2018 | Refsnaes et al. | |
| 2018/0255091 A1* | 9/2018 | Mestha | H04L 63/1416 |
| 2018/0321692 A1* | 11/2018 | Castillo-Effen | G06T 19/003 |
| 2018/0322699 A1* | 11/2018 | Gray | G06T 19/003 |
| 2018/0348987 A1 | 12/2018 | Sawaki | |
| 2019/0005195 A1* | 1/2019 | Peterson | G16H 10/60 |
| 2019/0087544 A1* | 3/2019 | Peterson | G16H 50/20 |
| 2019/0102494 A1 | 4/2019 | Mars | |
| 2019/0198169 A1* | 6/2019 | T | G06F 16/951 |
| 2019/0266295 A1* | 8/2019 | Masuda | G06Q 50/40 |
| 2019/0294975 A1* | 9/2019 | Sachs | H04W 56/00 |
| 2020/0012265 A1* | 1/2020 | Thomsen | G06F 3/0481 |
| 2020/0118053 A1* | 4/2020 | Chapin | G06Q 10/06315 |
| 2020/0159876 A1* | 5/2020 | Hsu | G06Q 50/04 |
| 2020/0250683 A1* | 8/2020 | Padmanabhan | G06Q 20/38215 |
| 2020/0265329 A1* | 8/2020 | Thomsen | G06N 5/048 |
| 2020/0358782 A1* | 11/2020 | Hager | G06F 21/645 |
| 2020/0377074 A1* | 12/2020 | Bekan | G01C 21/3691 |
| 2021/0140290 A1* | 5/2021 | Eslinger | E21B 43/128 |

FOREIGN PATENT DOCUMENTS

| | | |
|---|---|---|
| JP | 2009-162597 A | 7/2009 |
| JP | 2017-211913 A | 11/2017 |
| JP | 2018-205951 A | 12/2018 |
| WO | 2018183275 A1 | 10/2018 |

OTHER PUBLICATIONS

European Patent Application No. 19932177.9, Extended European Search Report mailed Nov. 30, 2022, 10 pages.

Japanese Patent Application No. 2021-524643, Office Action mailed May 23, 2023.

* cited by examiner

(1) COMMUNICATION WITH FUTURE OR PAST SELF

(2) COMMUNICATION WITH PERSON WHO DOES NOT ACTUALLY EXIST (3) COMMUNICATION BETWEEN PEOPLE VIA VIRTUAL DTs (4) COMMUNICATION IN A GROUP (5) COMMUNICATION BETWEEN GROUPS

FIG.5

DIGITAL TWIN COMPUTING APPARATUS, DIGITAL TWIN COMPUTING METHOD, PROGRAM AND DATA STRUCTURE

CROSS-REFERENCE TO RELATED APPLICATIONS

This application is a U.S. National Stage Application filed under 35 U.S.C. § 371 claiming priority to International Patent Application No. PCT/JP2019/022765, filed on 7 Jun. 2019, the disclosure of which is hereby incorporated herein by reference in its entirety.

TECHNICAL FIELD

The present invention relates to a digital twin computing apparatus, a digital twin computing method, a program, and a data structure.

BACKGROUND ART

A technology called a digital twin has conventionally been known. Digital twins are used mainly in the field of manufacturing and the like, and refer to digital information obtained by reproducing an actual object (e.g., a part of a machine or the like) in a digital space. It is possible to keep track of a phenomena that occur in the actual object in real time and the like by using a digital twin, and therefore, for example, digital twins have been utilized in product quality improvement and the like. Note that PTL 1 discloses a technique for determining behavior of a moving object.

CITATION LIST

Patent Literature

[PTL 1] Japanese Patent Application Publication No. 2017-211913

SUMMARY OF THE INVENTION

Technical Problem

However, a conventional digital twin is digital information obtained by reproducing an actual object in a digital space, and has not been directed toward reproducing an actual living creature (including a human) in a digital space. Also, a conventional digital twin is a reproduction of an object that exists in reality, and consideration has not been given to, for example, performing computation for fusing digital twins, exchanging portions of constituent elements between digital twins, and the like, to expand digital twins of objects and living creatures that do not actually exist.

It is thought that by expanding the target range of digital twins to objects and living creatures that do not actually exist and performing simulation and the like using these digital twins, it is possible to assist new value creation, problem solving of various problems, and the like.

The embodiments of the present invention have been made in view of the foregoing points and aim to expand the target range of digital twins.

Means for Solving the Problem

In order to achieve the above-described aim, a digital twin computing apparatus according to an embodiment of the present invention is characterized by including a memory and a processor configured to store, in a storage, a first digital twin in which at least one model defining at least one function of an entity at a given time, and at least one piece of second data that includes, as a constituent element, first data for realizing the function of the entity due to being input to the model are included, create at least one second digital twin by performing predetermined first computation using, as a computation target, at least one first digital twin stored in the storage, and execute computation for arranging the second digital twin in a sandbox for which a predetermined time axis has been set, and realizing a function of an entity indicated by the second digital twin in the sandbox in accordance with the time axis.

Effects of the Invention

It is possible to expand the target range of digital twins.

DESCRIPTION OF EMBODIMENTS

Hereinafter, an embodiment of the present invention will be described. The embodiment of the present invention will describe a digital twin computing apparatus 10 that can create digital twins of objects and living creatures that do not actually exist by performing a predetermined computation (this computation is expressed as "digital twin computing") on digital twins not only for objects in the target range of digital twins but also for living creatures (including people).

Note that hereinafter, a digital twin created through digital twin computing will be expressed as "virtual digital twin" or "virtual DT". On the other hand, a digital twin serving as a computation target of digital twin computing will be expressed as "digital twin" or "DT".

Here, although a digital twin of an object or a living creature that exists in reality is envisioned as a digital twin serving as a computation target of digital twin computing, there is not necessarily a limitation to this, and digital twins of objects and living creatures that do not exist in reality (e.g., digital twins of fictional products, digital twins of fictional characters, digital twins of deceased people, etc.) may also be included. Also, objects may include not only tangible objects (e.g., machines, vehicles, buildings, workpieces, materials, natural objects, etc.), but also intangible objects (e.g., electricity, light, heat, etc.). Furthermore, living creatures may also include animals (including humans), fungi, plants, archaea, and bacteria, as well as viruses and the like. Note that hereinafter, objects and living creatures will also be referred to collectively as "entities".

The digital twin computing apparatus 10 according to the embodiment of the present invention can arrange a virtual DT in a virtual space-time called a sandbox, and realize various simulations and services by performing sandbox execution computation (i.e., computations for advancing time or reversing time).

Definition of Terms

Hereinafter, definitions of terms to be used in the embodiment of the present invention will be described.

- Digital twin or DT: digital information reproducing an entity (object or living creature); realized using at least one model and at least one piece of data that includes data that can be input to these models in a configuration. A digital twin is provided with an ID (digital twin ID) for identifying the digital twin. Also, information indicating whether the digital twin expresses an object or a living creature is associated with the digital twin as an attribute. Note that hereinafter, a model for realizing a digital twin will also be expressed as "DT model", and data that includes data that can be input to the DT model in a configuration will also be expressed as "DT data".

- DT model: digital information by which a specific function of a digital twin (i.e., behavior of the digital twin, a change of state, etc.) at a given time is defined. A DT model uses DT data corresponding to the DT model as input and outputs the result of processing for realizing the specific function. The DT model is provided with an ID (model ID) for identifying the DT model in the digital twin (accordingly, a DT model is uniquely identified using a set composed of a digital twin ID and a model ID). For example, a pre-defined function, a rule-based model, an estimation model created using a method such as machine learning, or the like can be used as these DT models.

- DT data: data for realizing a specific function of a digital twin at a given time. These pieces of DT data are collected by, for example, sensing an entity with a sensor or the like. The DT data is associated with a model ID of a DT model that uses the DT data as input. Note that the DT data may also be associated with multiple model IDs (i.e., a certain piece of DT data may also be the input of multiple DT models). The DT data may also include data that is not input to the DT model (e.g., a digital twin ID, etc.).

- Virtual digital twin or virtual DT: digital information created by performing digital twin computing on a digital twin; arranged in a sandbox. Similarly to a digital twin, a virtual digital twin is realized using at least one DT models and at least one piece of DT data that includes data that can be input to these DT models in a configuration. Also, a virtual digital twin is associated with the sandbox in which the virtual DT is arranged, and is provided with an ID (virtual digital twin ID) for identifying the virtual DT in the sandbox.

- Digital twin computing: computation for creating a virtual digital twin based on a digital twin. Digital twin computing can be roughly divided into three computations, namely "setting computation", "duplication computation", and "fusion computation". For example, duplication computation creates at least one virtual digital twin by copying a digital twin as-is. Duplication computation may also be computation for further creating a virtual digital twin based on a virtual digital twin. The details of these computations will be described later.

- Sandbox: Virtual space-time in which a virtual DT is arranged. Due to sandbox execution computation being performed, a virtual DT arranged in the sandbox is executed (i.e., DT data is input to the DT model of the virtual DT according to change over time, and a specific function is realized by the DT model). The sandbox is provided with an ID (sandbox ID) for identifying the sandbox.

- Sandbox execution computation: Computation for executing a sandbox. Due to the sandbox execution computation, the time in the sandbox changes, and the virtual DT is executed according to that change.

Overall Configuration

Figure 1:
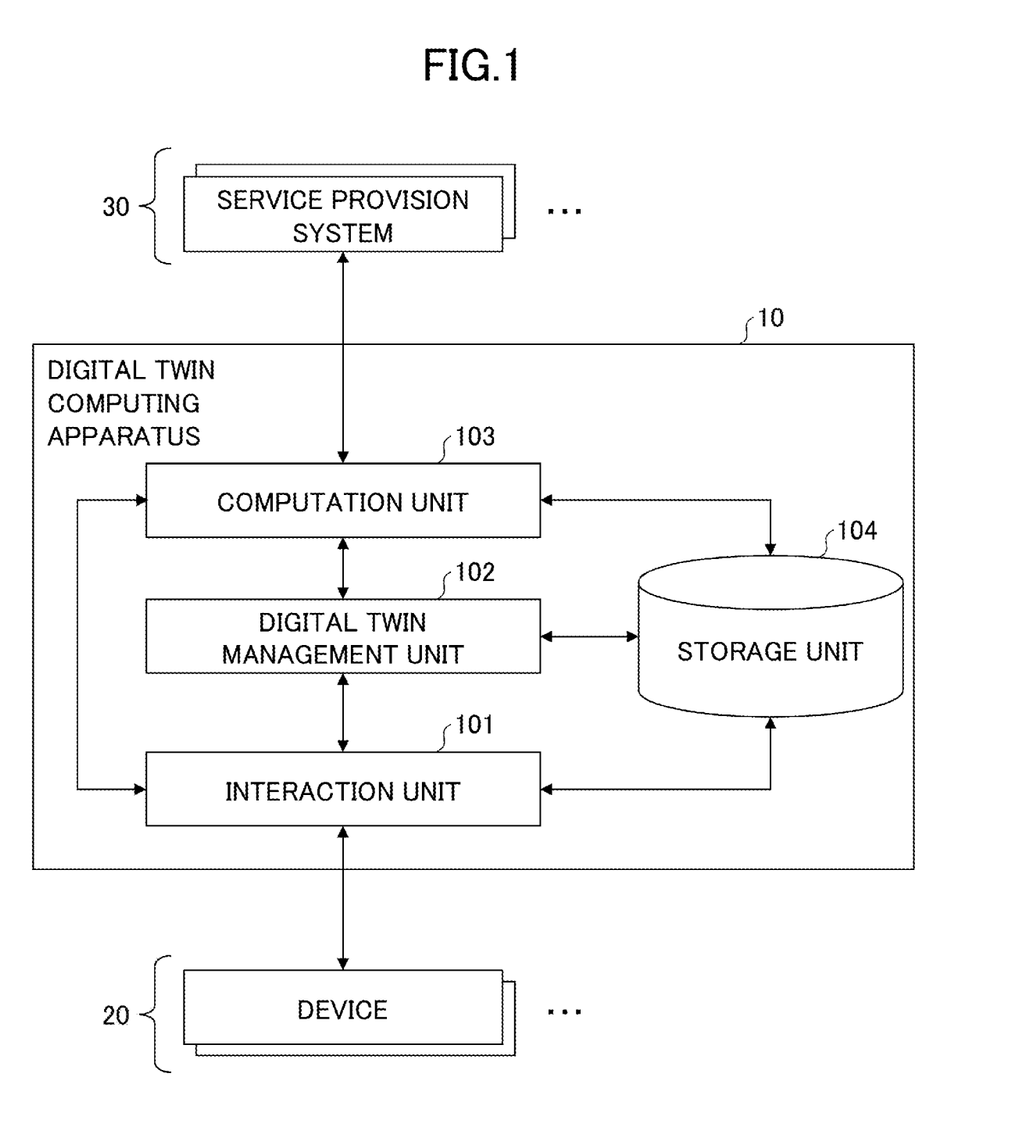
FIG. 1 is a diagram illustrating an example of an overall configuration of a digital twin computing apparatus according to an embodiment of the present invention.

Next, an overall configuration of a digital twin computing apparatus 10 according to an embodiment of the present invention will be described with reference to FIG. 1. FIG. 1 is a diagram illustrating an example of an overall configuration of the digital twin computing apparatus 10 according to an embodiment of the present invention.

As illustrated in FIG. 1, the digital twin computing apparatus 10 according to the embodiment of the present invention includes an interaction unit 101, a digital twin management unit 102, a computation unit 103, and a storage unit 104.

The interaction unit 101 collects data from a device 20, and outputs data indicating the sandbox execution results (or the results of each type of processing performed during execution of the sandbox) as feedback information to the device 20. At this time, the interaction unit 101 may also perform conversion processing such as converting the data collected from the device 20 into a predetermined data format, or converting the collected data into a data format corresponding to the device 20 before outputting the data to the device 20. That is, the interaction unit 101 may also convert the data collected from the device 20 into a data format that can be input to the DT model of the digital twin or convert the collected data into a data format that can be input to the device 20 before outputting the data to the device 20.

Here, the device 20 from which data is collected by the interaction unit 101 is various types of devices that acquire various information from an object, a living creature, an environment, or the like in the real world. Specific examples thereof include various types of sensors for sensing an entity or an environment, a smartphone used by a person, a digital camera that captures an image of an environment in the surrounding area or the like of an object or a living creature, a wearable device worn by a living creature such as a person, a vehicle-mounted device used in a case where the object is a vehicle, and a control device for controlling another device (also includes a Brain-Machine Interface (BMI) that controls another device using brainwaves of a person or the like). Examples of the information acquired from these devices 20 include bodily information of a person (features including physical appearance and shape, such as height and weight, and involuntary states such as heart rate, blood pressure, brain waves, body heat, and amount of perspiration), psychological information (emotions, thoughts, psychological state, etc.), activity information (voluntary activities and actions such as bodily movement, hand movement, and walking speed, speech, etc.), entity information (social attributes such as age, sex, nationality, and occupation, relationships with other people such as family relationships and co-worker relationships, records, etc.), and environmental information of the surrounding area environment of a person (temperature, humidity, weather, meteorological phenomena, and the like of surrounding area environment). On the other hand, although the information acquired from an object differs according to the type or the like of the object, if the object is a car, examples of the information include bodily information (features including physical appearance and shape, such as shape and body weight, internal states such as engine rotation rate and temperature, etc.), psychological information (emotions of personification=agent, etc.), activity information (states that can be observed from outside of the entity, such as speed and position information, activity, actions, and behavior), entity information (social attributes such as manufacturer, car type, manufacturing country, owner, passengers, etc.), and environmental information of the surrounding area environment of the car (number of cars in the surrounding area, temperature, humidity, temperature, meteorological phenomena, etc.).

On the other hand, the device 20 to which the data is output by the interaction unit 101 is various types of devices that control an entity that actually exists or an environment or provides some sort of information to the entity. Specifically, examples thereof include control devices that control various types of machines (a vehicle, a manufacturing apparatus, a robot, etc.), a display that provides an image to a person or the like, a speaker that provides audio to a person or the like, a VR device that provides a Virtual Reality (VR) environment to a person or the like, and a control device (also includes a BMI) that controls another device. The data output to these devices 20 is data indicating the sandbox execution result (or the result of various types of processing performed during execution of the sandbox), and examples thereof include control information obtained based on a result of simulation performed in the sandbox, prediction information obtained based on a result of simulation performed in the sandbox, and audio information uttered by the virtual DT in the sandbox.

Note that the data collected by the interaction unit 101 (or data obtained by converting the data format of the data) is stored in the storage unit 104 as DT data. At this time, the interaction unit 101 stores the DT data in the storage unit 104 in association with a digital twin ID of a digital twin for which the DT data is stored. Furthermore, the DT data may also be provided with an identifier and may be stored in the storage unit 104 in association with a set composed of the digital twin ID of the digital twin and the DT data ID of the DT data. Note that the DT data ID is an ID for identifying the DT data.

Also, data indicating the sandbox execution result (or the result of various types of processing performed during execution of the sandbox) is stored in the storage unit 104 by a later-described computation unit 103. Accordingly, the interaction unit 101 reads out data indicating the sandbox execution result (or the result of various types of processing performed during execution of the sandbox) from the storage unit 104, and outputs (e.g., transmits via a communication network) the read-out data to the device 20.

The digital twin management unit 102 manages the digital twin stored in the storage unit 104. Here, digital twins of various entities are stored in the storage unit 104. As described above, the digital twins are realized by at least one DT model and at least one piece of DT data.

For example, the digital twin of a certain person is realized using a personality model in which the personality of the person is defined, a thought/behavior model in which the thoughts and behavior of the person is defined, a capability model in which the capability of the person is defined, and the DT data for these DT models. In this manner, a digital twin of a person is realized using DT models in which the personality, thoughts, behavior, capability, and the like of the person are defined, and the DT data to be input to these DT models (e.g., bodily information, psychological information, activity information, entity information, environment information, etc.). Note that in addition to these, various DT models may also be included in the digital twin of a person.

The above-described personality model, thought/behavior model, and capability model may also be realized using DT models of more specific concepts. For example, the personality model may also be realized by a character model in which the character of the person is defined, and a values model in which the values of the person are defined. Similarly, for example, the thought/behavior model may also be realized by an emotion model in which the emotions of the person are defined, and a behavior trend model in which a behavior trend of the person is defined. Similarly, for example, the capability model may also be defined by a knowledge model in which the knowledge of the person is defined, a language model in which the language capability of the person is defined, and a perception model in which the perception of the person is defined. Note that these DT models may also be realized using DT models of even more specific concepts. That is, the DT models for realizing the digital twin may also have a tiered structure.

Note that the digital twins of all people do not need to be realized by the same DT models. For example, the digital twin of a given person may also be realized using a personality model, a thought/behavior model, and a capability model, whereas the digital twin of another given person may be realized using a personality model and a thought/behavior model.

Also, times are included as parameters in the digital twin. Accordingly, one digital twin can realize a function at a given time using the time as a parameter. Here, as described above, the data collected by the interaction unit 101 (or data obtained by converting the data format of the data) is stored in the storage unit 104 as DT data.

Accordingly, the digital twin stored in the storage unit 104 is updated accompanying a change in the state of the actual entity corresponding to the digital twin. For example, a heart rate measured by an actual person is stored in the storage unit 104 as DT data in association with the digital twin ID of the digital twin of the person. Accordingly, the digital twin is updated to a digital twin in which the heart rate of the actual person is reflected.

Note that the storage unit 104 stores various information relating to the digital twins. Examples of such information include information for identifying an actual entity corresponding to a digital twin (e.g., a user ID, object ID, etc.), a relationship with another digital twin (e.g., there being a completed product-component relationship between a digital twin and another digital twin, there being a host-parasite relationship between a digital twin and another digital twin, etc.), the data format of the DT data input to the DT model for realizing the digital twin, and the data format of the data output by the DT model. Although these pieces of information can be defined using any format, for example, ontology can be used.

In response to a request from a service provision system 30, the computation unit 103 creates a virtual DT by performing digital twin computing or arranges these virtual DTs in a sandbox and performs sandbox execution computation. The service provision system 30 is a server or a group of servers that provide a service using data indicating a sandbox execution result, data indicating a result of various types of processing performed during execution of the sandbox, and the like.

Figure 2:
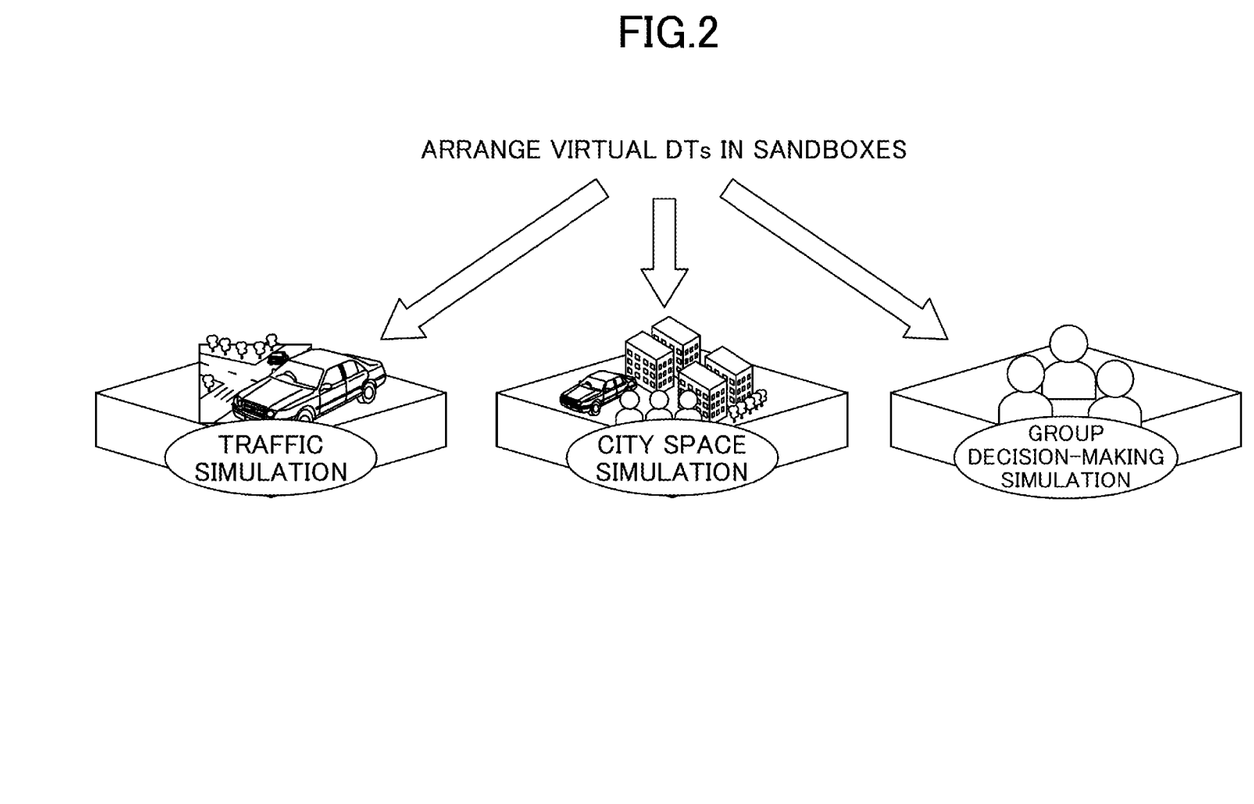
FIG. 2 is a diagram for illustrating an example of execution of a sandbox.

Here, various simulations can be performed by arranging a virtual DT in the sandbox and executing the sandbox. For example, as illustrated in FIG. 2, a traffic simulation can be performed by creating virtual DTs such as cars, people, and streets and arranging them in the sandbox. Also, for example, as illustrated in FIG. 2, a city space simulation can be performed by creating virtual DTs of buildings and people and arranging them in the sandbox. Also, for example, as illustrated in FIG. 2, a group decision-making simulation can be performed by creating virtual DTs of people, arranging them in the sandbox, and causing the people to perform desired decision-making. Note that these are examples, and it is possible to perform various simulations by arranging virtual DTs in a sandbox and executing the sandbox.

Accordingly, various services using the result of such a simulation, information on the execution process, and the like are conceivable as services provided by the service provision system 30. Examples thereof include Mobility as a Service (MaaS), an automatic driving service, a distribution service, a smartphone provision service, and an android communication service.

Digital twins are stored in the storage unit 104 as described above. Also, times are associated with a digital twin, and at least a digital twin of a time indicating the current time is stored in the storage unit 104. However, digital twins of times indicating the past in addition to the time indicating the current time may also be stored in the storage unit 104. That is, for example, the history of the digital twin from after the creation of the digital twin to the current time may also be stored in the storage unit 104. In this case, the digital twins may also have different or identical DT models and DT data according to the time. For example, a past digital twin and a current digital twin of a given person may have different capability models and DT data that is input to the capability model.

The data indicating the sandbox execution result and the data indicating the result of each type of processing during execution of the sandbox are also stored in the storage unit 104. In addition to these, various pieces of data that are needed for execution of the sandbox and the like are stored in the storage unit 104.

Note that although the history of the digital twin is stored in the storage unit 104, there are also cases in which association with a time is not needed if the attribute of the digital twin is an "object". For example, if the digital twin does not change or may be deemed as unchanging even if the time changes (e.g., a digital twin of a building, a mountain, or a planet, or the like), association with a time is not needed. However, even in this case, depending on the simulation performed in the sandbox, there are also cases in which it is necessary to store the digital twin in the storage unit 104 in association with a time. For example, there are cases in which simulation is performed in the sandbox using a time axis of several hundred years or several thousand years to the present, and the like.

Note that the configuration of the digital twin computing apparatus 10 illustrated in FIG. 1 is an example, and may also be another configuration. For example, the digital twin computing apparatus 10 may also be constituted by a first apparatus including the interaction unit 101, a second apparatus including the digital twin management unit 102 and the storage unit 104, and a third apparatus including the computation unit 103.

Digital Twin Computing

As described above, digital twin computing is computation for creating a virtual DT based on a digital twin. Digital twin computing can be largely divided into three computations, namely "setting computation", "duplication computation", and "fusion computation". "Setting computation" refers to computation for creating a virtual DT that sets the DT model and the DT data of a digital twin at a given time (or computation for setting the DT model and the DT data of the digital twin at a given time to be a virtual DT that has already been created). "Duplication computation" refers to computation for creating a virtual DT by copying the DT model and the DT data of a digital twin at a given time. "Fusion computation" refers to a computation for creating a virtual DT obtained by combining the DT model and DT data of a digital twin at a given time.

Also, "setting computation" can be divided into three computations, namely "setting", "exchange", and "anonymization". "Setting" refers to the most basic computation of "setting computation", and is computation for setting the DT model and the DT data of the digital twin at a given time as-is as the virtual DT (or computation for setting the DT model and the DT data of the digital twin at a given time as-is as an already-created virtual DT). "Exchange" refers to computation for creating a virtual DT obtained by exchanging the DT models and DT data between multiple digital twins. "Anonymization" is a special case of "setting", and refers to computation for anonymizing the DT data relating to the entity information among the DT data copied in the virtual data, according to a provided anonymization condition. Note that in the actual method of anonymization, for example, the DT data relating to information and entity information that can identify the entity may also be processed and deleted, and the virtual DT may also be prevented from being able to access the DT data relating to the information and entity information that can identify the entity. Furthermore, anonymization may also be realized by performing processing for adding noise to the DT data, processing such as switching the DT data, or processing that is a combination of these types of processing, based on an index such as the usefulness or anonymity required for the virtual DT and the simulation performed using the virtual DT.

Note that when a virtual DT is created through digital twin computing, the virtual DT may also be created by copying the DT model and the DT data of the digital twin, and the virtual DT may also be provided with right of access to the DT model and the DT data of the digital twin being computed.

Figure 3A:
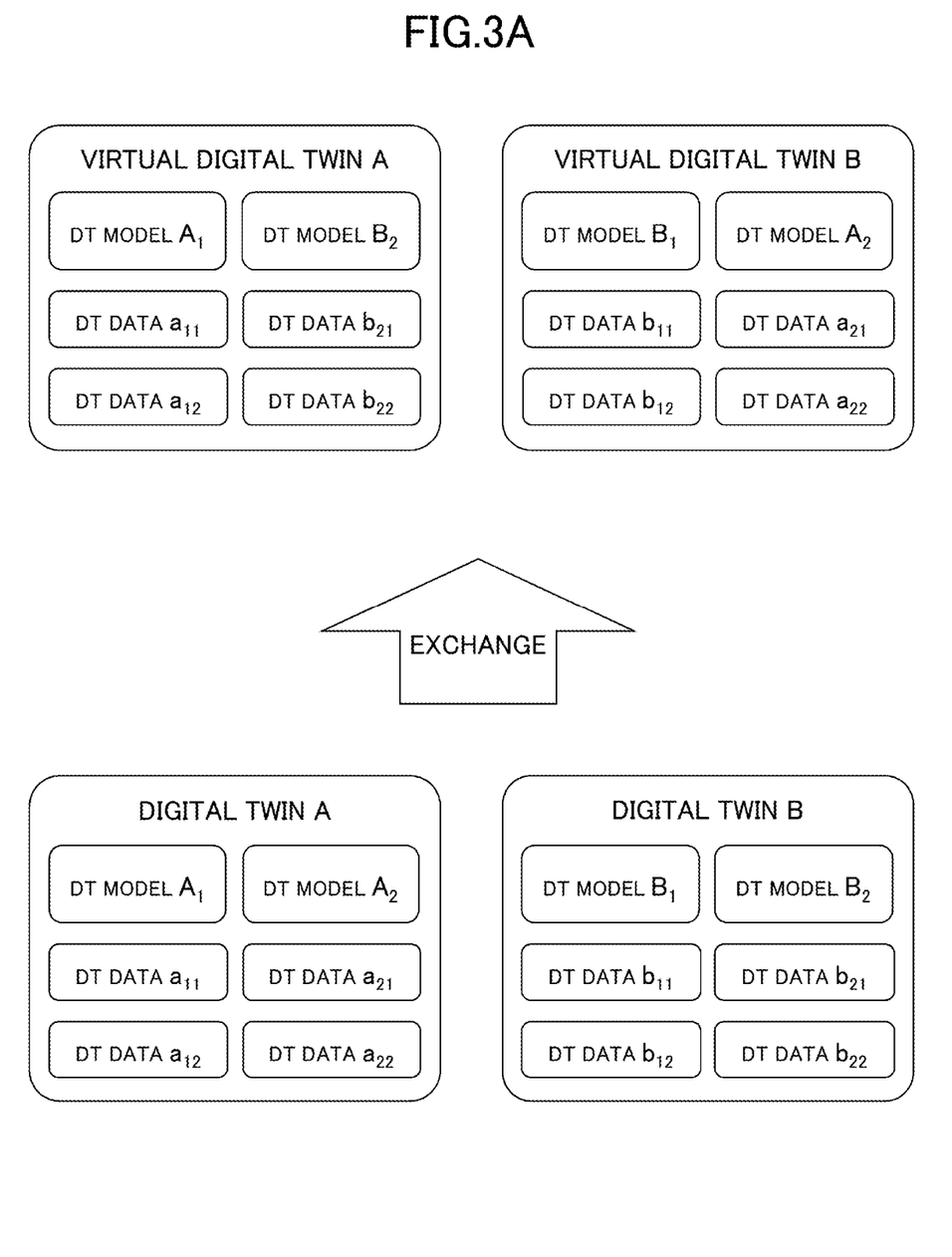
FIG. 3A is a diagram for illustrating an example of digital twin computing (exchange).

Here, "exchange", which is one "setting computation" of digital twin computing, will be described with reference to FIG. 3A. FIG. 3A is a diagram for illustrating an example of digital twin computing (exchange).

As illustrated in FIG. 3A, the digital twins being computed are "digital twin A" and "digital twin B". The digital twin A is realized using a DT model $A_1$, a DT model $A_2$, DT data $a_{11}$, DT data $a_{12}$, DT data $a_{21}$, and DT data $a_{22}$. Also, the digital twin B is realized using a DT model $B_1$, a DT model $B_2$, DT data $b_{11}$, DT data $b_{12}$, DT data $b_{21}$, and DT data $b_{22}$.

At this time, in "exchange computation", which is one "setting computation" of digital twin computing, the virtual DT is created by exchanging the DT models and DT data between the digital twin A and the digital twin B. For example, a virtual digital twin A that is realized using the DT model $A_1$, the DT model $B_2$, the DT data $a_{11}$, the DT data $a_{12}$, the DT data $b_2$, and the DT data $b_{22}$, and a virtual digital twin B that is realized using the DT model $B_1$, the DT model $A_2$, the DT data $b_{11}$, the DT data $b_{12}$, the DT data $a_{21}$, and the DT data $a_{22}$ are created.

Accordingly, it is possible to create a virtual DT obtained by exchanging some functions between multiple digital twins. For this reason, for example, it is possible to create virtual DTs obtained by switching capability models between multiple people and perform simulation using those virtual DTs, or the like.

Note that the DT models and DT data that realize the virtual DTs are designated as computation conditions of "exchange" computation. That is, the DT models and the DT data that are to be exchanged between the digital twin A and the digital twin B to create the virtual DTs are designated as computation conditions of "exchange" computation. Also, in the example illustrated in FIG. 3A, a case was shown in which the virtual DTs are realized using the DT models and the DT data, but as described above, the virtual DT may also be provided with right of access to the DT models and the DT data.

Figure 3B:
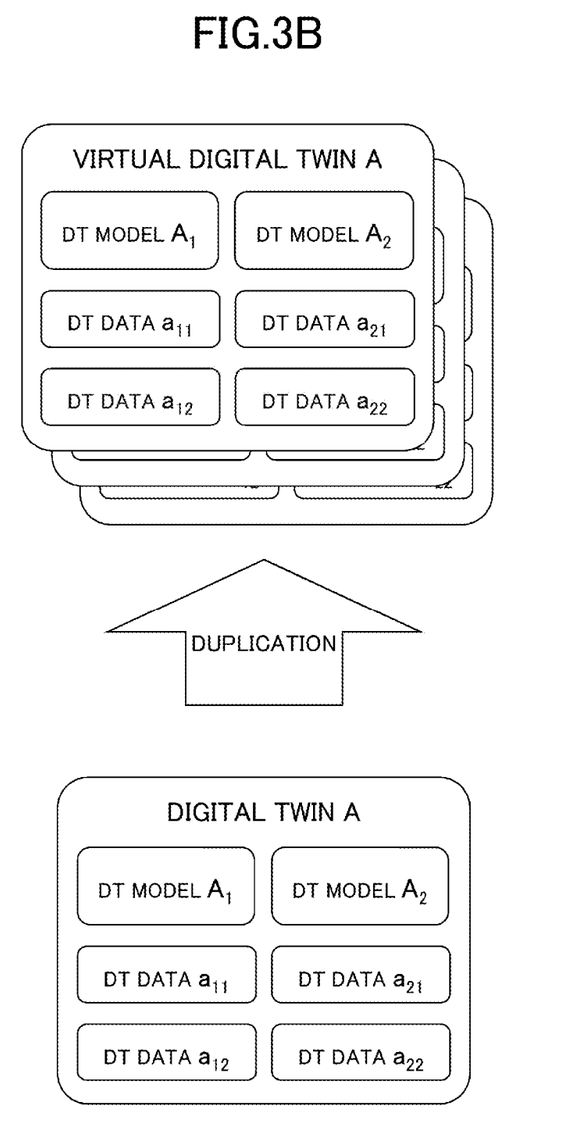
FIG. 3B is a diagram for illustrating an example of digital twin computing (duplication).

Next, "duplication computation" of digital twin computing will be described with reference to FIG. 3B. FIG. 3B is a diagram for illustrating an example of digital twin computing (duplication).

As illustrated in FIG. 3B, it is assumed that, using a digital twin being subjected to computation as "digital twin A", the digital twin A is realized using the DT model $A_1$, the DT model $A_2$, the DT data $a_{11}$, the DT data $a_{12}$, the DT data $a_{21}$, and the DT data $a_{22}$.

At this time, in "duplication computation" of digital twin computing, one or more virtual DTs obtained by copying the DT models and the DT data of the digital twin A as-is are created. In the example illustrated in FIG. 3B, a case is shown in which three virtual DTs are created.

This makes it possible to create one or more virtual DTs obtained by duplicating one digital twin. For this reason, for example, it is possible to perform a simulation in which multiple virtual DTs are created based on a digital twin of a given person, and these virtual DTs are caused to debate with each other (that is, a simulation in which a debate is held by identical people).

Note that the number of virtual DTs to be created is designated as a computation condition of "duplication computation". Also, in the example illustrated in FIG. 3B, a case was shown in which the virtual DTs are realized using the DT models and the DT data, but as described above, the virtual DTs may also be provided with access rights to the DT models and the DT data.

Figure 3C:
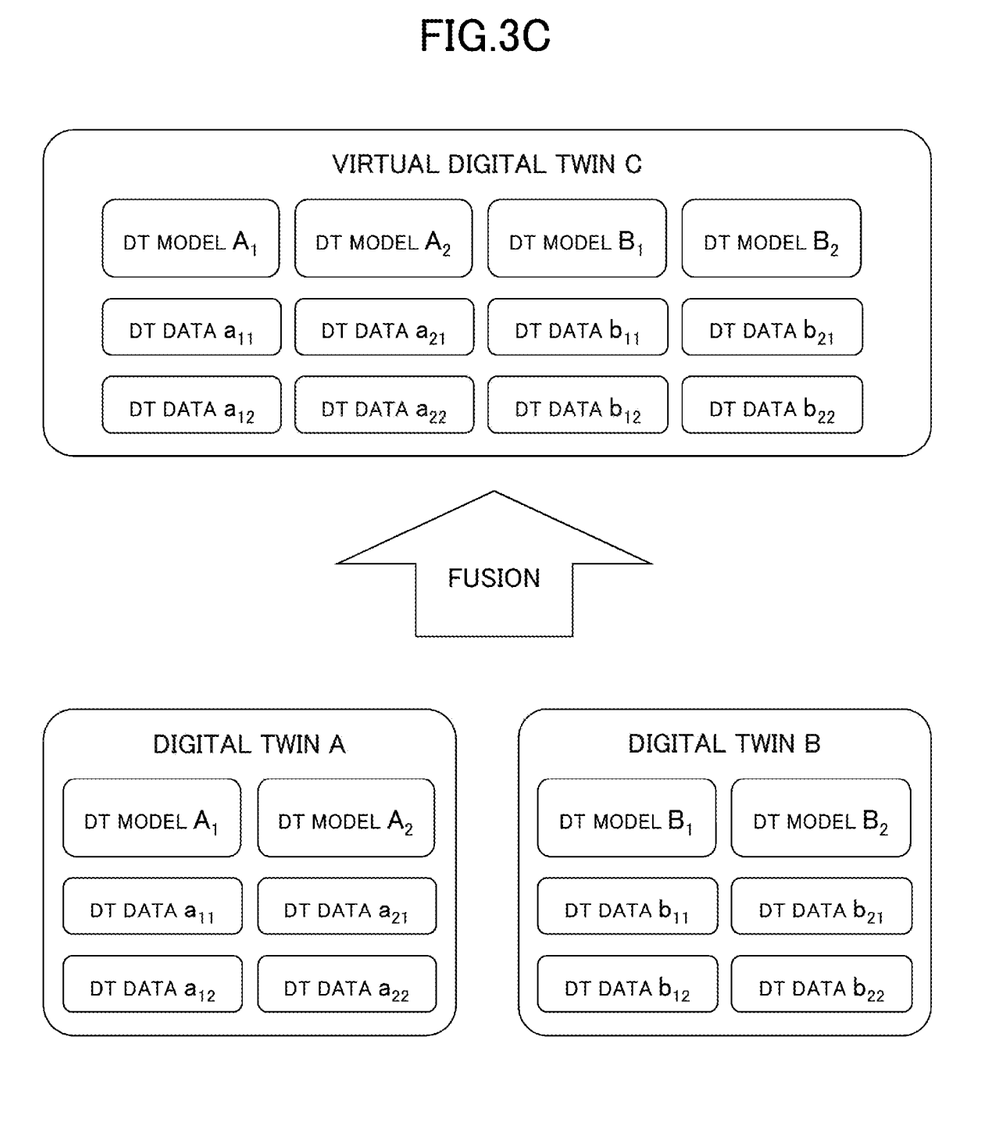
FIG. 3C is a diagram for illustrating an example of digital twin computing (fusion).

Next, "fusion computation" of digital twin computing will be described with reference to FIG. 3C. FIG. 3C is a diagram for illustrating an example of digital twin computing (fusion).

As illustrated in FIG. 3C, the digital twins being computed are "digital twin A" and "digital twin B". The digital twin A is realized using a DT model $A_1$, a DT model $A_2$, DT data $a_{11}$, DT data $a_{12}$, DT data $a_{21}$, and DT data $a_{22}$. Also, the digital twin B is realized using a DT model $B_1$, a DT model $B_2$, DT data $b_{11}$, DT data $b_{12}$, DT data $b_{21}$, and DT data $b_{22}$.

At this time, in "fusion computation" of digital twin computing, the virtual DT is created by fusing the DT models and DT data of the digital twin A and the DT models and DT data of the digital twin B. That is, for example, a virtual digital twin C is created which is realized using the DT model $A_1$, the DT model $A_2$, the DT model $B_1$, the DT model $B_2$, the DT data $a_{11}$, the DT data $a_{12}$, the DT data $a_{21}$, the DT data $a_{22}$, the DT data $b_{11}$, the DT data $b_{12}$, the DT data $b_{21}$, and the DT data $b_{22}$.

This makes it possible to create a virtual DT obtained by fusing the functions of multiple digital twins. For this reason, for example, it is possible to create a virtual DT of a virtual person obtained by fusing capabilities of multiple people, perform simulation using that virtual DT, or the like.

Note that in the example illustrated in FIG. 3C, a case was described in which two digital twins are fused, but regarding the number of digital twins being subjected to computation, any number can be designated as a computation condition of "fusion computation". Furthermore, the DT models and DT data of the digital twins to be fused into the virtual DT may also be designated separately as computation conditions of "fusion computation". Also, in the example illustrated in FIG. 3C, a case was shown in which the virtual DT is realized using DT models and DT data, but as described above, the virtual DT may also be provided with right of access to the DT models and the DT data.

Also, in "fusion computation" of digital twin computing, instead of handling simple DT models and DT data as-is, it is also possible to create new DT models and new DT data using the DT models and the DT data of the original digital twins and use them as the DT models and the DT data of the virtual DT. Specifically, in addition to the above-described processing illustrated in FIG. 3C, a new DT model C1 can be created based on the DT data of the digital twin A and the DT data of the digital twin B. That is, the DT model C1 and the DT model C2 may be created using the DT data $a_{11}$, the DT data $a_{12}$, the DT data $a_{21}$, the DT data $a_{22}$, the DT data $b_{11}$, the DT data $b_{12}$, the DT data $b_{21}$, and the DT data $b_{22}$, DT data such as DT data $c_{11}$ obtained by selecting from the DT data $a_{11}$ and the DT data $b_{11}$ and DT data $c_{22}$ obtained by selecting from the DT data $a_{22}$ and the DT data $b_{22}$ may be created, and a virtual digital twin C realized using these DT models and DT data may be created.

As described above, digital twin computing is computation for creating a virtual DT based on digital twins, but second virtual twin computing for creating a virtual DT based on virtual DTs may be further defined. That is, second "setting computation" may be computation for creating another virtual DT obtained by setting DT models and DT data of virtual DTs of a given time (or computation for setting DT models and DT data of virtual DTs of a given time in a virtual DT that has already been created), second "duplication computation" may be computation for creating another virtual DT by copying DT models and DT data of virtual DTs of a given time, and second "fusion computation" may be computation for creating another virtual DT obtained by combining the DT models and DT data of virtual DTs of a given time. Digital twin computing of second "setting", second "exchange", and second "anonymization" is also similarly computation performed based on a virtual DT instead of a digital twin.

Also, "deletion" computation may be defined as computation for deleting a virtual DT in second digital twin computing.

Sandbox Execution Processing

Figure 4:
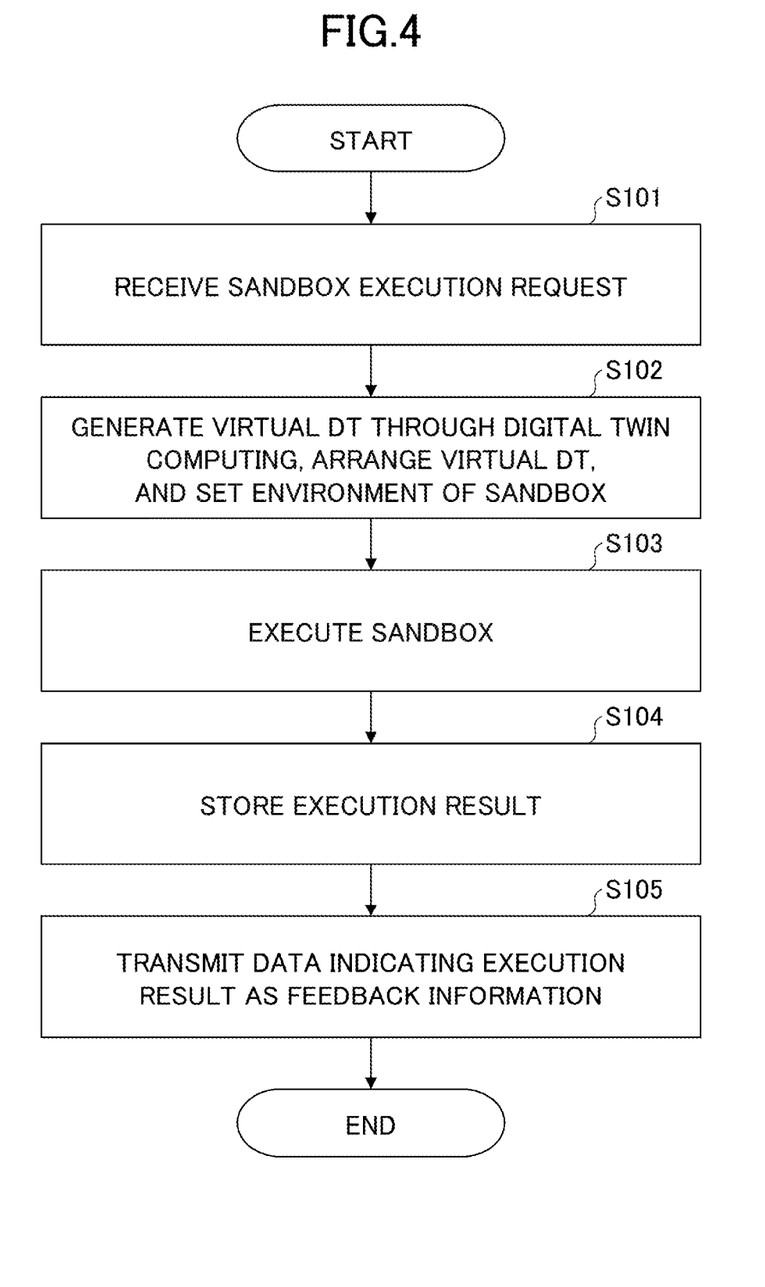
FIG. 4 is a flowchart illustrating an example of sandbox execution processing.

Next, processing (sandbox execution processing) that is performed when a virtual DT is created and arranged in a sandbox and then the sandbox is executed will be described with reference to FIG. 4. FIG. 4 is a flowchart illustrating an example of sandbox execution processing.

Step S101: First, the computation unit 103 receives a sandbox execution request from the service provision system 30. Various types of conditions relating to execution of the sandbox are designated in the sandbox execution request. These conditions are, for example, conditions indicating what kind of virtual DT is to be arranged in the sandbox and the start time and end time of performing execution computation.

Note that a predetermined template may also be prepared as the sandbox, and an ID or the like indicating the template may be designated in the above-described execution request. Examples of templates include a template for a sandbox indicating modern-day Japan, a template for a sandbox indicating Japan at a point in time in the past (e.g., the year 1900), a template for a sandbox in which Japan at a point in time in the future (e.g., the year 2300) is predicted, and a template for a sandbox in which a fictional space-time is set. Accordingly, for example, since it is possible to arrange the virtual DT in a sandbox prepared as a template and to execute the sandbox, it is possible to simplify the information designated in the sandbox execution request.

Step S102: Next, the computation unit 103 generates a virtual DT from a digital twin through digital twin computing based on the condition designated in the sandbox execution request. Then, the computation unit 103 arranges the computed virtual DT in the sandbox and sets the environment of the sandbox. The environment of the sandbox includes, for example, the start time and end time for when the sandbox is to be executed, the speed of time (e.g., the speed and advancing direction of time), and the like. Note that the speed of time refers to the speed with which time progresses in the sandbox, and it is possible to speed up or slow down the time relative to that of the real world.

In addition to these, various things may also be set as the environment of the sandbox according to the aim of performing simulation in the sandbox. Examples of the environment of the sandbox include repeatedly executing a certain time range until a certain condition is satisfied, and stopping the elapse of time in the sandbox until the DT data satisfying a certain condition is collected from the device 20.

Here, when the virtual DT is to be created, a virtual DT created using some of the DT models and DT data of a digital twin (i.e., a simple virtual DT using only some of the functions of a digital twin) may be created. In this manner, for example, a virtual DT including only the functions needed for the simulation may be created. Accordingly, it is possible to reduce the amount of calculation, the data capacity, and the like needed to execute the sandbox. Note that if the DT model has a tiered structure, provisional DT models (e.g., DT models functioning as stubs or mocks, etc.) need only be defined as the DT models of more specific concepts or DT models of broader concepts when DT models of more specific concepts or DT models of broader concepts for the DT models that realize the functions needed for simulation are needed.

Step S103: Next, the computation unit 103 executes the sandbox. That is, the computation unit 103 performs sandbox execution processing to change the time of the sandbox and change the behavior, state, and the like of the virtual DTs according to the change in time. Note that the behavior, state, and the like of the virtual DTs are expressed as the output of the DT model by inputting the DT data to the DT model of the virtual DT.

Here, the data to be collected in real time from the device 20 by the interaction unit 101 (or the data obtained by converting the data format of the data) may be used as the DT data input to the DT models of the virtual DTs, DT data collected from the device 20 in the past may also be used, and DT data created as appropriate, or for example, DT data indicating various types of conditions and fictional information obtained through setting computation for the virtual DT designated during the sandbox execution request by the service provision system 30, and the like may also be used. Alternatively, for example, data collected in real time may be used as a portion of the DT data, DT data collected from the device 20 in the past may be used as the other portion of the DT data, and the like.

Note that for example, in the following typical sandbox execution aims, the following time axes and DT data are used.

If the sandbox execution aim is future prediction: A time axis for the future is set, and the sandbox execution computation is performed from a certain time in the future to any time. At this time, DT data indicating fictional information of the future is input to the virtual DTs arranged in the sandbox.

If the sandbox execution aim is past verification: A time axis for the past is set in the sandbox, and sandbox execution processing is performed from a certain time in the past to any time. At this time, data collected in the past from the device 20 is input as the DT data to the virtual DTs arranged in the sandbox.

If the sandbox execution aim is current-state analysis: A time axis including the current point in time is set, and the sandbox execution calculation is performed from a certain time in the past or the current time to any time. At this time, data collected in the past from the device 20 or data collected in real time is input as the DT data to the virtual DTs arranged in the sandbox.

If the sandbox execution aim is consultation regarding a certain topic of discussion: Any time axis is set in the sandbox, and the sandbox execution computation is performed from a given time. At this time, any data is input as the DT data in the virtual DTs arranged in the sandbox, and sandbox execution computation is performed until the conclusion of the consultation converges or achieves equilibrium.

If the sandbox execution aim is discussion with a virtual DT: Any time axis is set in the sandbox, and the sandbox execution computation is performed from a given time. At this time, the data collected in real time from the device 20 is input as the DT data to the virtual DTs arranged in the sandbox, and data indicating the processing result of the virtual DTs (e.g., if the DT data is data indicating an utterance, the DT data is a response to the utterance, etc.) is repeatedly transmitted to the user of the device 20 as feedback information.

Step S104: Next, the computation unit 103 stores the data indicating the sandbox execution result in the storage unit 104. That is, the computation unit 103 stores data indicating the result obtained after execution of the sandbox ends in the storage unit 104 in association with the sandbox ID of the sandbox.

Here, the computation unit 103 also stores the data indicating the results of the processing performed during execution of the sandbox in the storage unit 104 in association with the sandbox ID. The data indicating the results of the processing performed during execution of the sandbox refers to data indicating the behavior, state, and the like of the virtual DT at each time in the sandbox, or the like. The data indicating the behavior, state, and the like of the virtual DTs is stored in the storage unit 104 in association with the virtual digital twin ID as well as the sandbox ID. Note that the time at which the processing was performed (time in the sandbox) is also further associated with the data indicating the results of the processing performed during execution of the sandbox.

In this manner, the data indicating the processing results of the times in the sandbox and the final execution results of the sandbox are stored in the storage unit 104. In other words, snapshots at each time from the start time to the end time of the sandbox are stored in the storage unit 104.

Step S105: Finally, the interaction unit 101 transmits the data stored in the storage unit 104 (data indicating the execution result of the sandbox, data indicating the results of the processing performed during execution of the sandbox, or both) to the device 20 as feedback information. Here, for example, the device 20 refers to a device 20 that is to be provided with a service provided by the service provision system 30 that transmitted the sandbox execution request in step S101 above.

Here, the interaction unit 101 may also perform mediation of the feedback information based on policy information stored in the storage unit 104 when the feedback information is to be transmitted to the device 20. Policy information is control information for preventing an adversely effect on the device 20 that received the feedback information, or on the user of the device 20. Examples of cases in which there is an adverse effect on the device 20 include a case in which the device 20 breaks down or the like due to an allowable limit on the device 20 being exceeded, and examples of cases in which there is an adverse effect on the user of the device 20 include a case in which the health or the like of the user of the device 20 is damaged.

If feedback information that violates the policy information is to be transmitted to the device 20, for example, the interaction unit 101 may perform changing, formatting, restriction, or the like of the feedback information in accordance with the policy information, may prevent the feedback information from being transmitted to the device 20, and may warn the device 20 before transmitting the feedback information. Note that examples of performing changing, formatting, restriction, or the like of the feedback information in accordance with the policy include multiplying a value included in the feedback information by an appropriate weight (e.g., a weight that is 0 or more and 1 or less), restricting the value included in the feedback information to an upper limit value or a lower limit value, or performing exclusion control between the values included in the feedback information.

Note that in step S105 above, although the feedback information was transmitted to the device 20, there is no limitation to this, and the interaction unit 101 may also transmit the feedback information to the service provision system 30. At this time, the interaction unit 101 may also transmit the feedback information to the service provision system 30 that is the transmission source that transmitted the sandbox execution request in step S101 above, and may also transmit the feedback information to another service provision system 30 that is different from that service provision system. Examples of cases in which the feedback information is transmitted to the other service provision system 30 include a case in which a series of services are provided through cooperation between a first service provided by the service provision system 30, and a second system provided by the other service provision system 30.

As described above, the digital twin computing apparatus 10 according to an embodiment of the present invention can create a virtual DT by performing digital twin computing on a digital twin of an entity (a person or an object), and perform various types of simulation in a sandbox using the virtual DT. At this time, the virtual DT may be a copy of the digital twin, or may be obtained by fusing multiple digital twins or exchanging some constituent elements. It is also possible not only to create the virtual DT by copying, fusing, and exchanging current digital twins, but also to create a virtual DT by copying, fusing, and exchanging past digital twins. During the simulation, it is also possible to use data collected in real time, data collected in the past, and data indicating fictional information.

For this reason, the digital twin computing apparatus 10 of the embodiment of the present invention can perform various types of simulation in the sandbox in which the virtual DTs are arranged, and can assist new value creation and problem-solving of various problems, and the like.

Note that in order to create a template for the above-described sandbox, a template creation function may be provided in which a digital twin stored in the storage unit 104 is searched for through a query using time, space, a range of space, entity information such as a social relationship, attributes of the digital twin, and the like, and a template is set by providing an ID indicating the template to the virtual DTs that designated all of the search results or a portion selected as appropriate. It is also possible to designate not only a street or a building in space, but also a relationship with a building or the like in space or a relationship with the space based on position information or a behavior history as a query for designating the template of the sandbox, and to set the digital twin of the living creature or object obtained as a result of the search as the virtual DT. It is also possible to set a virtual DT based on a portion of the tiers of a DT model or a portion of DT data of a digital twin obtained as a result of the search using the inside of the body of a human or the inner structure of an object as query, and it is also possible to set a virtual DT based on a digital twin obtained as a result of the search using an environmental condition such as the weather or weather conditions as a query.

The template for the sandbox may also include a function of changing or setting any time, space, or environmental condition as conditions of the virtual DT or the space-time of the sandbox, and furthermore, these times, spaces, and environmental conditions may also be set so as to be set or changed if the elapse of a certain amount of time or the state of the virtual DT matches a predetermined condition after the state of the simulation, or the like.

Furthermore, the template creation function may also include a digital twin computing function of applying digital twin computing to the digital twin and applying second digital twin computing to an existing sandbox or a template for a sandbox during creation of the sandbox or a template for the sandbox. The template creation function may also be used as a sandbox creation function by providing an ID indicating a sandbox instead of providing an ID indicating a template.

In this manner, setting tasks for performing various simulations can be reduced by enabling creation of a sandbox or a template for a sandbox.

APPLICATION EXAMPLES

Hereinafter, application examples of a digital twin computing apparatus 10 according to an embodiment of the present invention will be described.

Application Example 1

Figure 5:
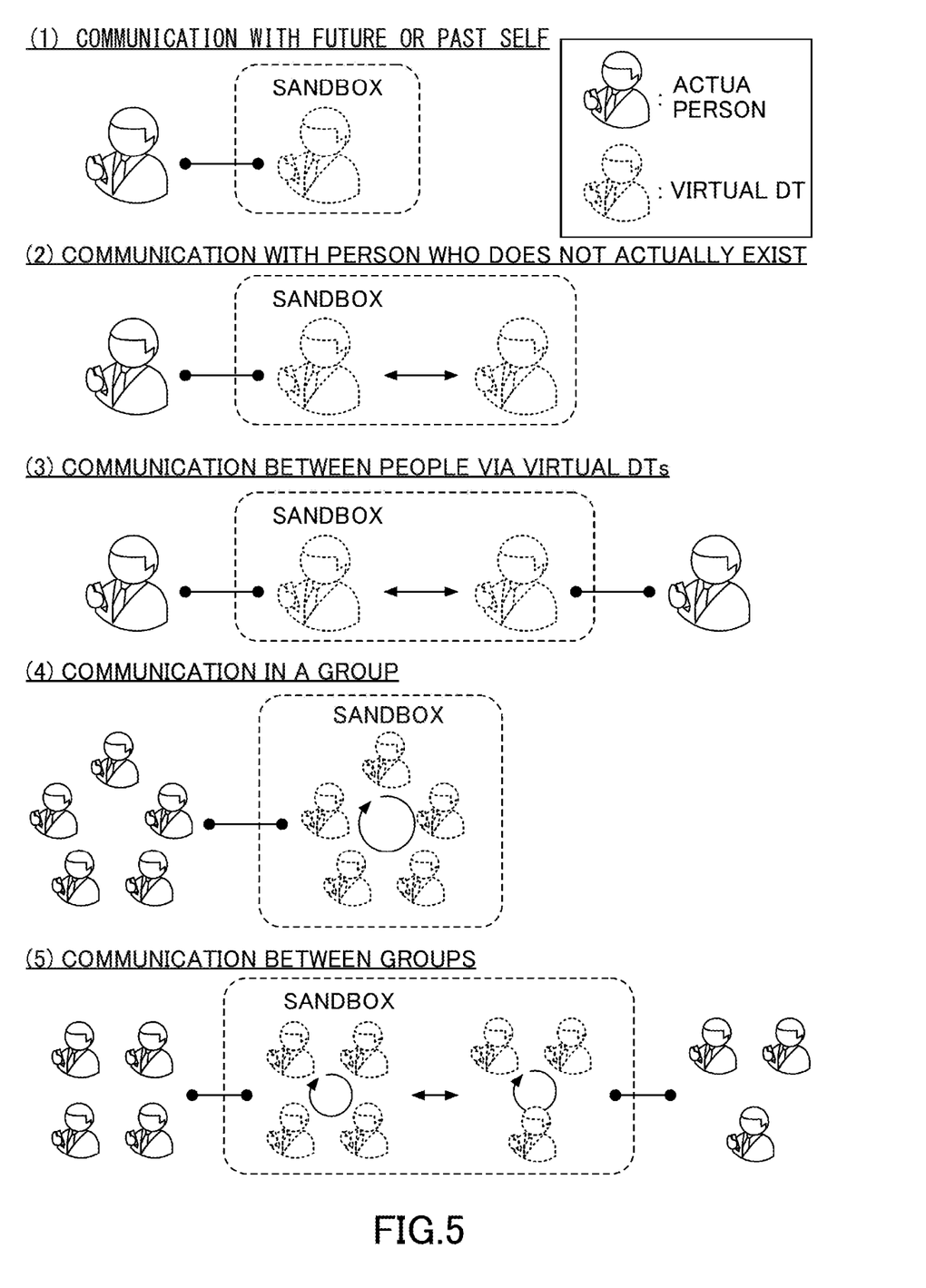
FIG. 5 is a diagram for illustrating an application example of applying the present invention to communication.

First, an example applied to communication using a virtual DT will be described with reference to FIG. 5. FIG. 5 is a diagram for illustrating an application example of applying the present invention to communication.

(1) The embodiment of the present invention can be applied to communication with a future or past self. That is, for example, a virtual DT is created through digital twin computing based on a digital twin of one's self at any time in the future or the past, and the virtual DT is arranged in a sandbox. Then, the sandbox is executed while data indicating one's own uttered content and the like are input to the virtual DT in real time as DT data. Accordingly, it is possible to have a discussion with one's past or future self, and for example, it is thought that this will be an opportunity for self-understanding and new discovery regarding one's self, and thus it is possible to prompt learning and growth. Note that in this case, it is possible to perform communication with another past or future person by creating a virtual DT based on a digital twin of another person instead of a digital twin of one's self.

(2) An embodiment of the present invention can be applied to communication with a person who does not actually exist. That is, for example, a virtual DT is created through digital twin computing based on the digital twin of a deceased person or a fictional character, and the virtual DT is arranged in the sandbox. Then, the sandbox is executed while data indicating one's own uttered content and the like are input to the virtual DT in real time as DT data. This makes it possible to have a discussion with a deceased person or a fictional character, and to utilize the experience of the deceased person or the fictional character, obtain new inspiration, satisfy a desire for communication, or the like.

Note that in this case, communication may be performed between a virtual DT corresponding to one's own digital twin and a virtual DT corresponding to the digital twin of the deceased person or the fictional character, and information indicating the result of the communication (or information indicating the process of communication) may be transmitted as feedback information to the device 20 used by an actual person.

(3) An embodiment of the present invention can be applied to communication between people performed via virtual DTs. That is, for example, virtual DTs are created through digital twin computing based on a digital twin of a given person and a digital twin of another given person respectively, and these virtual DTs are arranged in a sandbox. Then, the sandbox is executed while given DT data (e.g., past DT data, DT data indicating fictional information, DT data obtained based on data collected in real-time, etc.) is input to the virtual DTs, and data indicating the execution results (or data indicating the results of various types of processing performed during execution) and the like are transmitted as feedback information to the devices 20 used by actual people. Since communication between virtual DTs can be performed in the sandbox more rapidly than communication between the actual people, it is possible to immediately obtain a communication result. For this reason, for example, it is possible to cause the virtual DTs to debate a given topic in advance, cause the virtual DTs to exchange knowledge, or the like, and it is possible to assist communication of intention between actual people, assist mutual understanding, and the like.

(4) An embodiment of the present invention can be applied to communication performed in a group. That is, virtual DTs are respectively created through digital twin computing based on digital twins of people belonging to a given group, and the virtual DTs are arranged in a sandbox. Then, the sandbox is executed while given DT data (e.g., past DT data, DT data indicating fictional information, DT data obtained based on data collected in real-time, etc.) is input to the virtual DTs, and data indicating the execution results (or data indicating the results of various types of processing performed during execution) and the like are transmitted as feedback information to the devices 20 used by the people belonging to the group. Accordingly, it is possible to cause the virtual DTs to debate a given topic in advance, cause the virtual DTs to perform knowledge exchange, cause the group to perform consensus building, perform optimization of the group, and the like, and it is possible to assist communication of intentions in the actual group, assist mutual understanding, and the like.

(5) An embodiment of the present invention can be applied to communication performed between groups. That is, for example, respective virtual DTs are created through digital twin computing based on digital twins of people belonging to a given group and digital twins of people belonging to another given group, and these virtual DTs are arranged in the sandbox. Then, the sandbox is executed while given DT data (e.g., past DT data, DT data indicating fictional information, DT data obtained based on data collected in real-time, etc.) is input to the virtual DTs, and data indicating the execution results (or data indicating the results of various types of processing performed during execution) and the like are transmitted as feedback information to the devices 20 used by the people belonging to the groups. Accordingly, for example, it is possible to cause the virtual DTs to debate a given topic in advance, cause the virtual DTs to perform knowledge exchange, cause the groups to perform consensus building, perform optimization between the groups, and the like, and it is possible to assist communication of intentions between the actual groups, assist mutual understanding, and the like.

Application Example 2

The embodiment of the present invention can be applied to artificial experience, virtual testing, and the like. In an embodiment of the present invention, for example, a virtual DT that can also speak a foreign language can be created by creating, through "setting computation", a virtual DT obtained by setting a language model of a digital twin of a person who speaks a foreign language in a digital twin of a person who can only speak their native language. For this reason, it is possible to cause a person who can only speak their native language to artificially experience their self as a person who can also speak a foreign language by executing a sandbox. Also, for example, in an embodiment of the present embodiment, it is possible to create a virtual DT that can be experienced using an optical zoom function as one's own vision by creating, through "setting computation", a virtual DT obtained by setting DT models for realizing the optical zoom function of a camera in a digital twin of a person. For this reason, it is possible to cause a person to artificially experience an optical zoom function as their own vision by executing a sandbox.

Application Example 3

In an embodiment of the present invention, application is possible in which the height, skill, or the like of a person is experienced artificially or is incorporated in the control of a robot. For example, it is possible to create a virtual DT obtained by acquiring the skill of a professional sports athlete, the skill of a professional chef, or the like, by creating, through "setting computation", a virtual DT obtained by setting DT models of a digital twin of the professional sports athlete, the professional chef, or the like in a digital twin of one's self or a digital twin of a robot. For this reason, for example, it is possible to perform practice for improving one's own skill based on a difference in skill from a professional, and it is possible to perform control of a robot that has acquired a skill of the same level as the skill of a professional.

Hardware Configuration

Figure 6:
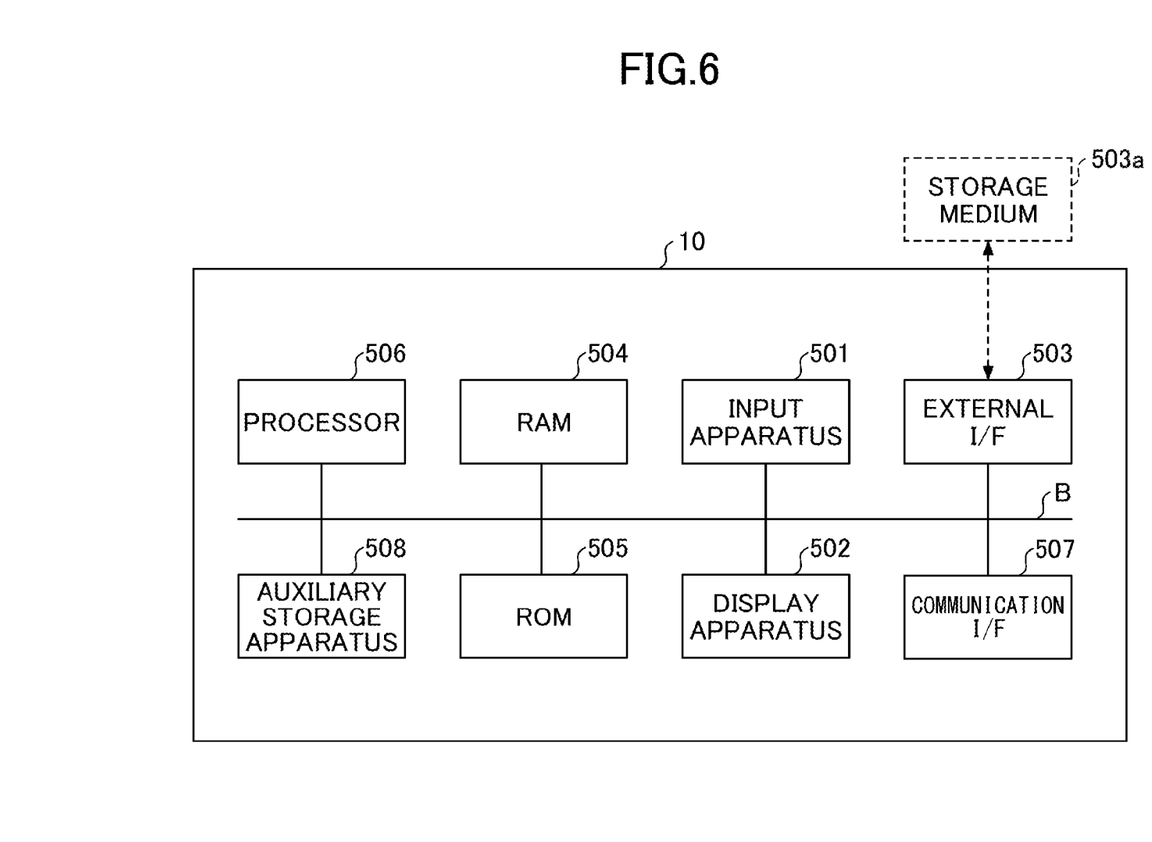
FIG. 6 is a diagram illustrating an example of a hardware configuration of a digital twin computing apparatus according to an embodiment of the present invention.

Lastly, a hardware configuration of the digital twin computing apparatus 10 according to an embodiment of the present invention will be described with reference to FIG. 6. FIG. 6 is a diagram illustrating an example of a hardware configuration of the digital twin computing apparatus 10 according to an embodiment of the present invention.

As illustrated in FIG. 6, the digital twin computing apparatus 10 according to an embodiment of the present invention includes an input apparatus 501, a display apparatus 502, an external I/F 503, a Random Access Memory (RAM) 504, a Read Only Memory (ROM) 505, a processor 506, a communication I/F 507, and an auxiliary storage apparatus 508. These pieces of hardware are communicably connected via a bus B.

The input apparatus 501 is, for example, a keyboard, a mouse, a touch panel, or the like. The display apparatus 502 is, for example, a display or the like. Note that the digital twin computing apparatus 10 may also not include at least one of the input apparatus 501 and the display apparatus 502.

The external I/F 503 is an interface with an external apparatus. Examples of the external apparatus include a storage medium 503a such as a CD, a DVD, an SD memory card, and a USB memory card. The digital twin computing apparatus 10 can perform reading, writing, and the like of the storage medium 503a via the external I/F 503. Note that the storage medium 503a may also store, for example, one or more programs for realizing the functional units of the digital twin computing apparatus 10 (the interaction unit 101, the digital twin management unit 102, the computation unit 103, etc.).

The RAM 504 is a volatile semiconductor memory. The ROM 505 is a non-volatile semiconductor memory. The processor 506 is, for example, various types of computing apparatuses such as a Central Processing Unit (CPU) and a Graphics Processing Unit (GPU). The functional units of the digital twin computing apparatus 10 are realized through, for example, processing for causing the processor 506 to execute the one or more programs stored in the auxiliary storage apparatus 508 and the like. Note that the processor 506 may also be, for example, an Field-Programmable Gate Array (FPGA) or the like.

The communication I/F 507 is an interface for connecting the digital twin computing apparatus 10 to a communication network. The one or more programs for realizing the functional units of the digital twin computing apparatus 10 may also be acquired (downloaded) from, for example, a predetermined server apparatus or the like via the communication I/F 507.

The auxiliary storage apparatus 508 is, for example, a storage apparatus such as a Hard Disk Drive (HDD) or a Solid State Drive (SSD). The auxiliary storage apparatus 508 includes, for example, an Operating System (OS), application programs for realizing various types of functions on the OS, one or more programs for realizing the functional units of the digital twin computing apparatus 10, and the like.

Also, the storage unit 104 of the digital twin computing apparatus 10 can be realized using the auxiliary storage apparatus 508. However, the storage unit 104 may also be realized using, for example, a storage apparatus or the like connected to the digital twin computing apparatus 10 via the communication network.

The digital twin computing apparatus 10 according to the embodiment of the present invention can realize the above-described various types of processing due to including the hardware configuration illustrated in FIG. 6. Note that although FIG. 6 illustrates a case in which the digital twin computing apparatus 10 according to an embodiment of the present invention is realized by one apparatus (computer), but there is no limitation to this. The digital twin computing apparatus 10 according to an embodiment of the present invention may also be realized by multiple apparatuses (computers). Also, one apparatus (computer) may also include multiple processors 506 and multiple memories (RAM 504, ROM 505, auxiliary storage apparatus 508, etc.).

The present invention is not limited to the above-described embodiments that were specifically disclosed, and various modifications, changes, combinations, and the like are possible without departing from the description of the claims.

REFERENCE SIGNS LIST

10 Digital twin computing apparatus
20 Device
30 Service provision system
101 Interaction unit
102 Digital twin management unit
103 Computation unit
104 Storage unit

The invention claimed is:

1. A digital twin (DT) computing apparatus comprising:
a memory; and
a processor configured to:
store, in the memory, a DT of an entity, the DT including at least one model defining at least one function of the entity at a given time;
receive a sandbox execution request including a kind of at least one virtual DT and a time duration of at least one simulation;
create a sandbox using a predetermined sandbox template for performing the at least one simulation using the at least one virtual DT;
create the at least one virtual DT of the DT according to the request and using only one or more functions of the at least one function needed for the at least one simulation;
collect entity data related to the entity;
input the entity data into a model included in the at least one virtual DT in accordance with a predetermined time axis of the sandbox;
perform the at least one simulation according to the time duration by arranging the virtual DT in the sandbox for which the predetermined time axis has been set and executing the sandbox;
store at least one result of executing the sandbox; and
transmit the at least one result.

2. The DT computing apparatus according to claim 1, wherein the processor is configured to create the at least one virtual DT by further:
setting at least one model and/or at least one piece of data included in the DT at the given time,
duplicating the at least one model and the at least one piece of data included in the DT at the given time, and
combining the at least one model and the at least one piece of data included in a plurality of DTs at the given time.

3. The DT computing apparatus according to claim 2, wherein the setting further includes exchanging a portion of models and a portion of data between a plurality of DTs, and anonymizing predetermined data included in the DT according to an anonymization condition.

4. The DT computing apparatus according to claim 1, wherein the processor is further configured to create at least one new virtual DT of at least one second DT.

5. The DT computing apparatus according to claim 1, wherein during the at least one simulation, the entity data is based on data collected in real time and predetermined data.

6. The DT computing apparatus according to claim 1, wherein the predetermined sandbox template is one of a plurality of predetermined sandbox templates.

7. The DT computing apparatus according to claim 1, wherein the request is received from a service provision system.

8. The DT computing apparatus according to claim 1, wherein the DT computing apparatus further includes a DT management unit and an interaction unit.

9. A digital twin (DT) computing method executed by a computer including a memory and a processor comprising:
    storing, in the memory, a DT of an entity, the DT including at least one model defining at least one function of the entity at a given time;
    receiving a sandbox execution request including a kind of at least one virtual DT and a time duration of at least one simulation;
    creating a sandbox using a predetermined sandbox template for performing the at least one simulation using the at least one virtual DT;
    creating the at least one virtual DT of the DT according to the request and using only one or more functions of the at least one function needed for the at least one simulation;
    collecting entity data related to the entity;
    inputting the entity data into a model included in the at least one virtual DT in accordance with a predetermined time axis of the sandbox;
    performing the at least one simulation according to the time duration by arranging the virtual DT in the sandbox for which the predetermined time axis has been set and executing the sandbox;
    storing at least one result of executing the sandbox; and
    transmitting the at least one result.

10. The DT computing method according to claim 9, wherein creating the at least one virtual DT further comprises:
    setting at least one model and/or at least one piece of data included in the DT at the given time,
    duplicating the at least one model and the at least one piece of data included in the DT at the given time, and
    combining the at least one model and the at least one piece of data included in a plurality of DTs at the given time.

11. The DT computing method according to claim 10, wherein the setting further includes
    exchanging a portion of models and a portion of data between a plurality of DTs, and
    anonymizing predetermined data included in the DT according to an anonymization condition.

12. The DT computing method according to claim 9, further comprising creating at least one new virtual DT of at least one second DT.

13. The DT computing method according to claim 9, wherein during the at least one simulation, the entity data is based on data collected in real time and predetermined data.

14. The DT computing apparatus according to claim 9, wherein the predetermined sandbox template is one of a plurality of predetermined sandbox templates.

15. A non-transitory computer-readable recording medium having stored therein a program for causing a computer including a memory and a processor to execute a digital twin (DT) computing method comprising:
    storing, in the memory, a DT of an entity, the DT including at least one model defining at least one function of the entity at a given time;
    receiving a sandbox execution request including a kind of at least one virtual DT and a time duration of at least one simulation;
    creating a sandbox using a predetermined sandbox template for performing the at least one simulation using the at least one virtual DT;
    creating the at least one virtual DT of the DT according to the request and using only one or more functions of the at least one function needed for the at least one simulation;
    collecting entity data related to the entity;
    inputting the entity data into a model included in the at least one virtual DT in accordance with a predetermined time axis of the sandbox;
    performing the at least one simulation according to the time duration by arranging the virtual DT in the sandbox for which the predetermined time axis has been set and executing the sandbox;
    storing at least one result of executing the sandbox; and
    transmitting the at least one result.

16. The non-transitory computer-readable recording medium according to claim 15, wherein creating the at least one virtual DT further comprises:
    setting at least one model and/or at least one piece of data included in the DT at the given time,
    duplicating the at least one model and the at least one piece of data included in the DT at the given time, and
    combining the at least one model and the at least one piece of data included in a plurality of DTs at the given time.

17. The DT non-transitory computer-readable recording medium according to claim 16, wherein the setting further includes
    exchanging a portion of models and a portion of data between a plurality of DTs, and
    anonymizing predetermined data included in the DT according to an anonymization condition.

18. The non-transitory computer-readable recording medium according to claim 15, further comprising creating at least one new virtual DT of at least one second DT.

19. The non-transitory computer-readable recording medium according to claim 15, wherein during the at least one simulation, the entity data is based on data collected in real time and predetermined data.

20. The non-transitory computer-readable recording medium according to claim 15, wherein the predetermined sandbox template is one of a plurality of predetermined sandbox templates.

* * * * *